United States Patent [19]

Carpenter et al.

[11] Patent Number: 4,823,623

[45] Date of Patent: Apr. 25, 1989

[54] DEVICE FOR TRANSFER OF FLUID INTO SEALABLE VIALS

[75] Inventors: Robert E. Carpenter, Nutley, N.J.; Robert D. Morrison, Madison, Wis.

[73] Assignee: Norton Company, Worcester, Mass.

[21] Appl. No.: 178,155

[22] Filed: Apr. 6, 1988

[51] Int. Cl.[4] .......................... G01N 1/20; G01N 1/10
[52] U.S. Cl. .............................. 73/864.74; 73/863.86
[58] Field of Search ............ 73/864.86, 864.87, 864.82, 73/864.63, 864.74, 863.85, 864.91, 864, 863.81, 863.86, 864.81, 864.51

[56] References Cited

U.S. PATENT DOCUMENTS

| | | | |
|---|---|---|---|
| 2,059,999 | 11/1936 | Rainville, Sr. | 73/864.63 |
| 2,255,369 | 9/1941 | Spaeth | 73/863.85 |
| 3,186,232 | 6/1965 | Yates et al. | 73/863.85 |
| 3,886,800 | 6/1975 | Boehringer | 73/864.82 |
| 4,000,654 | 1/1977 | Harris, Jr. | 73/863.81 |
| 4,452,091 | 6/1984 | Richers | 73/864.74 X |
| 4,517,851 | 5/1985 | Tice | 73/864.86 X |
| 4,625,574 | 12/1986 | Robbin | 73/864.63 |
| 4,644,807 | 2/1987 | Mar | 73/864.87 X |
| 4,651,574 | 3/1987 | Spencer | 73/864.74 X |
| 4,704,141 | 11/1987 | Krebber | 73/23.1 X |

FOREIGN PATENT DOCUMENTS

| | | | |
|---|---|---|---|
| 2907558 | 8/1980 | Fed. Rep. of Germany | 73/863.85 |
| 823950 | 4/1981 | U.S.S.R. | 73/864.63 |

OTHER PUBLICATIONS

DOPAK® brochure titled "Process Samplers"; 8 pages; by Dopak Inc. of Plainsboro, N.J. published by Apr. 1988.

Primary Examiner—Tom Noland
Attorney, Agent, or Firm—Walter Fred

[57] ABSTRACT

A fluid sample transfer device made of non-toxic inert material and preferably of virgin fluorocarbon material provides a sealed closed system for transferring a sample of the fluid to be analyzed for contaminants into a vial sealed by a self-sealing septum pierced by a pair of hypodermic needles of different length fixed to and extending from a bottom side of a body having a fluid inlet passage and a vent or outlet passage therein. A long needle is connected to the inlet passage and conveys fluid through and out its sharply pointed outlet end situated close to the bottom of a vial being filled therewith and a short hollow needle is connected to the outlet passage and extends to its pointed inlet end situated slightly below the septum of the vial to allow gas above the fluid filling the vial to escape. One embodiment is adapted for sealably connecting the upper portion of the body to a conventional bailer and has a valve for selectively preventing or allowing passage of fluid to the long needle and vial. Another embodiment is adapted to sealably connect the upper portion of the body to a bladder pump and to a filter device and has a valve for selectively preventing or allowing passage of fluid to either the long needle and vial or to the filter device. Guides may also be provided for guiding a vial into and out of sealing engagement with the needles and the body.

10 Claims, 1 Drawing Sheet

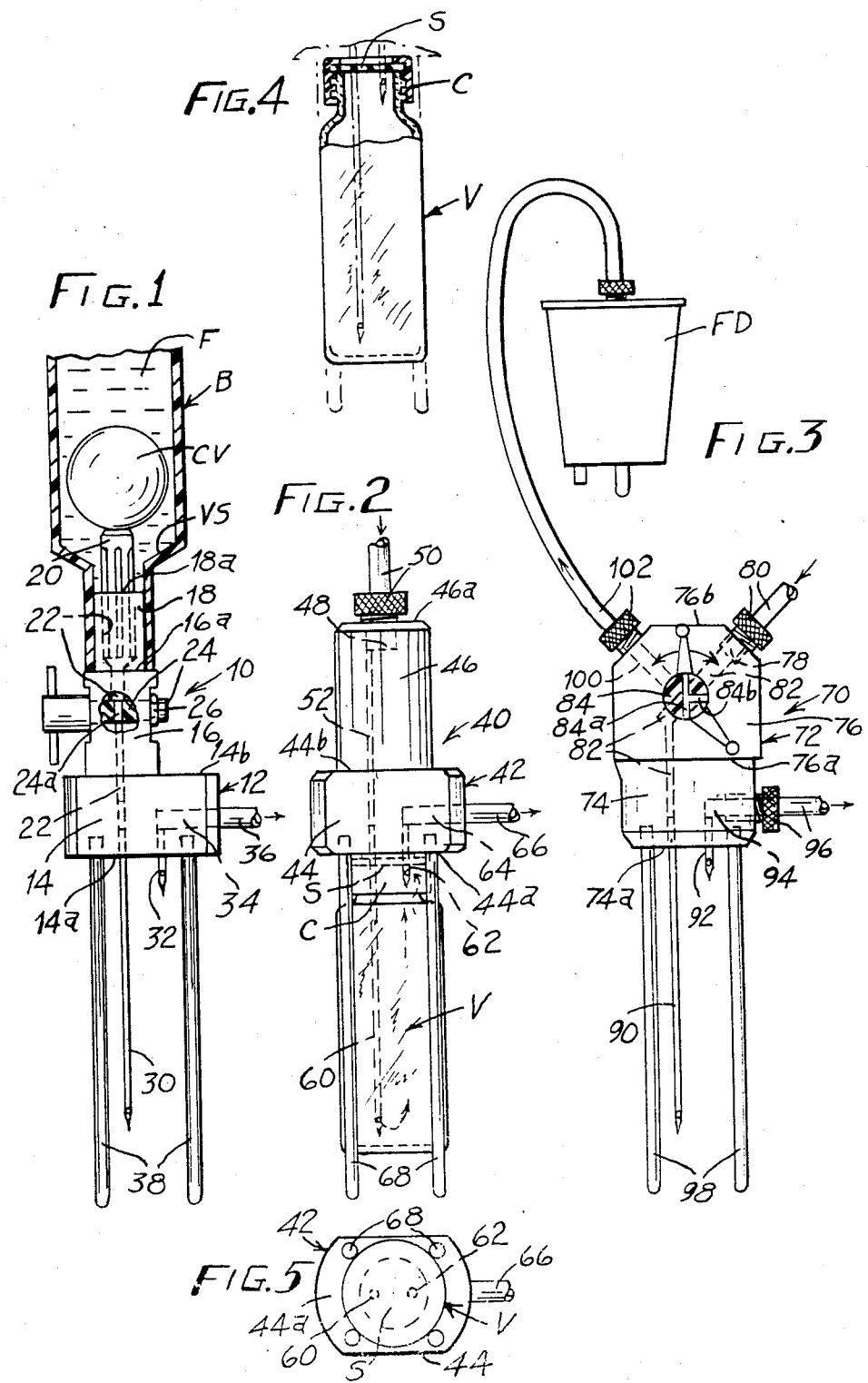

DEVICE FOR TRANSFER OF FLUID INTO SEALABLE VIALS

TECHNICAL DISCLOSURE

Devices made of inert nontoxic materials provide a closed sealed system for transferring a sample of fluid such as ground water taken from a reservoir or underground well by a bladder pump or bailer, into a self-sealing vial for a more precise analysis and detection of contaminants.

BACKGROUND OF THE INVENTION

1. Field of the Invention

The invention relates to devices for transferring a sample of liquid taken from underground wells, storage tanks, barrels, and reservoirs, by means of a bailer or bladder pump and the like into sealable vials for a more precise and accurate analysis of the contents thereof at the laboratory.

2. Description of the Prior Art

Heretofore, a sample of a body of liquid such as water to be analyzed for contaminants and toxic substances, has been obtained by lowering an empty vessel known as a bailer into the well or reservoir and when filled, withdrawing it to the surface. One such device which seals the sample between a septum cap and a ball check valve at opposite ends of the container is disclosed in U.S. Pat. No. 4,625,574.

Another liquid sampling device shown in U.S. Pat. No. 2,059,999, has upper and lower valve seals for sealing off the liquid sample contained therein.

Still another gas sampling device having an end sealed by a resilient septum pierced by a hyperdermic needle to withdraw and transfer a portion of the sample to an analyser, is disclosed in U.S. Pat. No. 3,886,800.

However, the applicants device differs in that it provides a sealed closed system by which a field sample of fluid can be immediately transferred directly from a larger source into one or more sealed vials of less volume. Thus, the sealed vials prevent escape of any of the original components or ingredients present in the original fluid sample and can be more accurately and effectively analyzed and tested for various contaminents by one or more laboratories.

SUMMARY OF THE INVENTION

A fluid sample transfer device made of inert non-toxic materials includes a main body having a fluid inlet passage extending from an inlet end at one side thereof to an outlet end at a bottom side of the body. An upper inlet end of a relatively long sharply pointed hollow inlet needle is fixed and connected to the outlet end of the inlet passage and extends a predetermined distance below the bottom side of the body.

A sealed valve movably mounted in the body provides means to selectively close or allow the flow of fluid through the fluid inlet passage. A second vent or exhaust passage extends through the body from an inlet end connected to the outlet end of a relatively short sharply pointed hollow outlet needle extending from the bottom side and situated closely adjacent and spaced from the larger inlet needle.

The upper side of the body has means for sealably connecting the inlet end portion of the inlet fluid passage to either the outlet end of a conventional bailer or a compression type fitting and tubing extending from a conventional bladder pump or the like connected to the source of fluid to be transferred.

Another embodiment provides a three way valve in the body by which fluid entering the fluid inlet passage may be closed off or diverted either to the longer needle and into the vial or to another filter inlet passage, compression fitting and tubing connected to a filtering device.

In all embodiments the transfer device may not be, but is preferably provided with a guide means fixed to and extending from the bottom side of the body for frictionally guiding a sealed vial and the self resealable resilient septum diaphram at the upper end of the vial into piercing sealing engagement with both the longer and short needles and bottom side of the body prior to opening the valve and transferring the fluid to the vial. Hence, the fluid enters and exits the sharp tip of the longer needle near the bottom of the vial and the air or gas above exits through the shorter needle whose tip is situated slightly below the resilient septum and allows the air or gas above the fluid to exit out the vent passage until the vial is full whereupon the valve is closed and the vial removed from the device.

BRIEF DESCRIPTION OF THE DRAWINGS

FIG. 1 is a view in elevation partly in section of one embodiment of the fluid transfer device of the invention adapted for insertion into the outlet end of a conventional fluid bailer device and raising the check valve off its seat to allow fluid flow into the transfer device.

FIG. 2 is a view in elevation of another embodiment of a fluid transfer device of the invention without a valve adapted for connection by a sealable compression fitting and tubing directly to a conventional bladder pump, not shown, connectable to the source of fluid to be transferred.

FIG. 3 is a view in elevation of still another embodiment of the fluid transfer in which a fluid inlet passage is connected by a compression fitting and tubing to a bladder pump connected to the source of fluid and a second fluid inlet passage is connected by a second compression fitting and tubing to a filtering device and a valve for selectively closing off or allowing the fluid to flow either to the longer needle or to the filtering device and the vent passage connected by a compression fitting and tube.

FIG. 4 is a view in elevation partly in section of a sealed vial including the resilient resealable septum diaphram retained by the cap screwed thereto, and, FIG. 5 is a bottom view of the transfer device of FIG. 2 showing the spaced guide means frictionally engaging and holding the vial in place during fluid transfer.

DESCRIPTION OF THE PREFERRED EMBODIMENT(S)

Referring to FIG. 1, a fluid transfer device has a main body 12 including an enlarged bottom portion 14 of predetermined axial thickness and diametral size extending upwardly from a relatively flat bottom surface or side 14a to an upper surface 14b. An intermediate valve containing portion or housing 16 extends upwardly from the surface 14b of the bottom portion 14 to an intermediate upper stop surface 16a that engages the lower outlet end surface of a conventional fluid or liquid bailer device B. An upper tubular portion 18 of the body 12 extends upwardly from surface 16a to an upper end surface 18a and is adapted to be inserted into and sealingly engage the internal outlet bore in the outlet end portion of the bailer B. An elongated externally grooved drain pin 20 is slidably inserted in an enlarged central internal fluid inlet passage or bore 22 in the upper portion 18.

The drain pin 20 extends upwardly a predetermined sufficient distance to an upper end thereof adapted to contact and raise the check valve CV off its valve seat VS in the bailer B and allow passage of fluid F to flow along the elongated grooves or passages in the pin 20 and inlet passage 22 to a reduced portion of the fluid inlet passage 22 adjacent to a two way rotary valve 24.

Rotary valve 24 is rotatably mounted in and extends axially through and sealingly engages the portion 16 of the body. A resilient O-ring 26 maintains and holds the valve 24 in sealing frictional engagement with the body 12. The valve 24 has a passage therethrough which when aligned with the passage 22, by rotating the valve, allows fluid to flow through the remaining lower reduced portion of the fluid passage 22 extending into the bottom portion 14 of the body 12. Connected with the passage 22 and extending downwardly from the bottom side 14a is a relatively long sharply pointed hollow needle 30 of predetermined length that is sightly less than the internal depth of a conventional size vial or vessel V shown in FIG. 4 to be pierced and filled with fluid F.

The upper inlet end of the hollow needle 30 is fixed to the bottom portion 14 in alignment with the fluid passage 22. Thus, the device provides a completely sealed closed system for fluid flow from the bailer B to and out the lower noncoring sharply pointed outlet end of the longer needle 30 and into a vial adjacent the body 12.

A second relatively short sharply pointed hollow outlet or vent needle 32 is also fixed to and extends downwardly a short distance below the bottom surface 14a of the portion 14 of the body 12. The short tubular gas outlet needle 32 has its upper outlet end connected to a fluid outlet passage 34 extending through and to one side of the lower portion 14 of the body 12 connected to a vent tube 36.

The length of the tubular vent needle 32 is such that the lower pointed inlet end portion of the needle 32 will pierce the septum of the vial and then project a relatively short distance below the septum sufficient to vent the gas above the fluid or liquid and provide a complete filling of the vial therewith.

Preferably, the device 10 is provided with guide means comprised of four elongated guide rails or tubes 38 fixed to and extending downwardly from the bottom side 14a and to ends beyond the pointed outlet end of the long needle 30. The guide means are adapted for frictionally engaging, holding, aligning, and guiding a typical 40 ml glass vial with a resealable septum membrane retained by a top cap into and out of piercing sealing engagement with both needles 30 and 32 during attachment and removal of the vial to and from the device 10.

To fill a vial with the sample fluid F taken with and contained in the bailer B, the upper portion 18 of the device 10 with the valve 24 closed is inserted into the outlet end bore of the bailer B. When seated against surface 16a the drain pin 20 raises the ball check valve CV off its seat VS and allows fluid to flow through inlet passage 22 to closed valve 24.

A vial such as shown in FIG. 4 is then inserted between the guide rails or tubes 38 and pushed upwardly until it contacts bottom surface 14a of the body 12 whereupon the inlet and outlet needles 30 and 32 have pierced and sealingly engaged the septum of the vial. Valve 24 is then opened allowing fluid F to flow through a completely closed and sealed system including passage 22 and into and out of the lower pointed end of needle 30 situated close to the bottom of the vial. Fluid or liquid F begins to fill the vial pushing the gas or air above it out the outlet needle 32 passage 34 and tube 36. When fluid F exits tube 36 the valve 24 is closed and the filled vial is immediately removed whereupon the needles are withdrawn and the septum reseals itself and seals the fluid sample contents therein for analysis.

Another embodiment of the invention is shown in FIGS. 2 and 5 comprising a fluid sample transfer device 40 adapted for a direct closed system attachment by a conduit extending to and from a bladder-type pump drawing the sample fluid from a reservoir or underground well or source of fluid or liquid.

The transfer device 40 comprises a main body 42 having an enlarged or lower bottom portion 44 extending upwardly from a bottom side or surface 44a to an upper surface 44b. An upper portion 46 extends from the upper surface 44b to an upper inlet end portion 46a provided with an internally threaded inlet end bore or passage 48 sealingly connected to a compression fitting and tube assembly 50 sealably connectable to a conventional bladder pump or other fluid sample container.

A fluid inlet passage 52 extends through the body 42 from the inlet bore 48 to the bottom side 44a of the lower portion 44. Fixed to the bottom portion 44 aligned with and connected to the passage 52 is the inlet end portion of a relatively long sharply pointed hollow needle 60 that extends through the upper septum S of the vial V and downwardly to a lower pointed outlet end portion situated close to the bottom of a conventional vial V shown in FIG. 4, and in contact with bottom side 44a of body 42.

A second relatively short sharply pointed hollow fluid outlet or vent needle 62 is fixed to and extends from the bottom portion 44 and through the septum S to a pointed inlet end thereof situated below and closely adjacent the septum diaphram or membrane S. The upper outlet end of the short vent needle 62 is connected to an outlet passage 64 extending to one side of the bottom portion 44 and connected to a vent tube 66. The vial V is in similar fashion previously described frictionally attached or held to the body 42 guided into and out of sealing engagement with the needles 60 and 62 by spaced guide means or guide rods 68 of relatively longer length than the long fluid inlet needle 60 which first pierces the septum S.

Filling the vial V requires placing the vial V between the guide rods 68 and pushing it upwardly into engagement with the bottom side 44a whereupon both needles 60 and 62 have pierced and sealingly engage the septum S. The pump connected between the tube 50 and source of fluid is then started whereby fluid passes through a sealed closed system including passage 52 and out inlet needle 60 and into the vial. Gas or fluid above the rising fluid exits the vial V through the outlet vent needle 62, passage 64, and vent tube 66. When the vial is filled and liquid begins to spill out the vent tube 66 the pump is shut off and the filled vial removed, whereupon the septum reseals itself and thus prevents escape of any of the components of the fluid contained therein prior to being analyzed.

A further embodiment of the invention shown in FIG. 3 comprises a fluid transfer device 70 including a main body 72 with a lower or bottom portion 74 extending upwardly from a bottom side or surface 74a to an enlarged upper valve containing portion or housing 76 extending upwardly from a lower surface 76a to oppositely beveled portions of an upper or top side 76b thereof.

One beveled portion of the top surface 76b is provided with an internally threaded fluid inlet bore or passage 78 adapted for connection to a compression fitting and tube assembly 80 extendable to and from a conventional bladder pump, not shown, normally connected to and pump fluid or liquid from a source thereof contained in a well reservoir or other container. The fluid inlet bore 78 connects to a fluid inlet passage 82 extending inwardly to and beyond a rotary valve 84 shown in closed position. A reduced portion of the inlet fluid passage 82 extends downwardly through the body 72 from the valve 84 to the bottom surface 74a of the lower portion 74 and is connected to the upper inlet end portion of a relatively long sharply pointed hollow fluid inlet needle 90 fixed to and extending from the lower portion 74. A relatively short sharply pointed hollow fluid outlet or venting needle 92 is also fixed to and extends downwardly from the bottom portion 74 to a pointed inlet end situated a predetermined distance from the surface 74a and spaced from the longer needle 90. An outlet passage 94 connects the short fluid exhaust needle 92 to a compression fitting and tubing assembly 96 threaded into the internally threaded outlet end portion of the outlet passage 94.

Guide means including guide rods or vials 98 extend from the lower portion 74 and provide means for attaching, holding, and guiding a vial V and septums thereon into and out of piercing sealing engagement with the needles and body 72.

On the opposite beveled portion of the oppositely beveled top side 76a of the upper portion 76 is a filter inlet port or passage 100 extending from the valve 84 to an internally threaded outlet end portion thereof sealably connected to a compression fitting and tube assembly 102 extending to and sealably connected to a conventional fluid or liquid filter FD by a similar compression tube fitting. Hence, valve 84 in the position shown prevents passage of fluid beyond the valve 84. However, rotating the valve 84 clockwise aligns a first passage 84a in the valve with the passage 82 and directs fluid flow to the longer needle and vial V to be filled. To filter the fluid the valve 84 is rotated counter-clockwise to position a second passage 84b in the valve in alignment with the inlet passage 82 and passage 84b in alignment with filter inlet passage 100. Hence, flow of liquid or fluid can be selectively diverted and directed to either the vial V or to the filtering device FD.

Operation of the device 70 for filling the vial V is similar to that of the previously described transfer devices 10 and 40. That is, the vial is inserted and positioned as before, either the valve 84 closed or opened prior to starting the bladder pump and pumping the fluid into the vial and either closing the valve 84 or stopping the bladder pump when the vial is filled and removing the sealed vial V to direct fluid to the filter FD requires either turning the valve 84 and starting the pump or first starting the pump and rotating the valve 84 to direct the flow to the filter FD.

Except for the hypodermic needles 30, 32, 60, 62, 90 and 92, the guide rods 38, 68 and 98, and the O-rings 26 retaining the rotary valves 24 and 84, all the other components of the transfer devices 10, 40 and 70, described hereinabove maybe made of any suitable nontoxic inert plastic, ceramic, or metallic material, for example, polyvinylchloride (PVC), polyethylene, glass, alumina, and stainless steel, but are preferably made of 100% virgin fluorocarbon materials such as polytetrafluoroethylene (PTFE), fluorinated ethylene propylene polymer (FETP).

The guide rods may also be made of other suitable fluorocarbons or non-toxic plastic materials but are preferably made of 316 stainless steel and have noncoring sharply pointed ends. The O-rings 26 may be made of any suitable resilient elastomer material such as natural or synthetic rubber or other elastic plastic material.

Shown in FIG. 4 is a typical vial V which can be utilized in conjunction with each of the transfer devices 10, 40, and 70, described hereinabove. The vial V is preferably a 40 ml volume glass vial of hollow or tubular cylindrical shape and predetermined diameter extending upwardly from an integral bottom to a neck and externally threaded open ended top portion. The top portion of the vial V has a relatively small annular top surface around its open end thereof that sealingly engages the septum made of suitable resilient self sealing non-toxic elastomer material held in sealing engagement with the top surface by an internally threaded cap C with a central opening therein for entrance of the needles.

Thus, the closed system transfer device of the invention reduces a potential bias with sampling volatile compounds in groundwaters during the transfer of the sample from the sampling device to the collection vial. During sample transfer, the sample may be subject to oxidation, volatilization, precipitation, and excessive agitation. These cumulative processes can result in redox and pH shifts which in turn can cause chemical transformations which can affect the results of the sample analysis. The sample can also become biased during filling of the collection vial by the entry of airborne contaminants and the inclusion of gas bubbles. Any of these sources of sample bias can be significant, especially when the contaminant of interest is in trace concentrations.

To address these potential biases, the sample transfer device of the invention was designed to complete a closed sampling system between a fluid sampling bailer pump and/or pump inlet and a collection vial or filter device. When operated properly, the device visibly displaces all of the gas from a 40 ml glass vial.

When the devices are used with a pump, the discharge rate should be reduced to at least 80 ml per minute to minimize sample agitation during filling. To draw a sample, the 40 ml vial is positioned within the four stainless steel guide posts and pushed along the posts until both needles puncture the septum. Liquid from the discharge line of the pump or end of the bailer then enters the vial through the longer needle and displaces the gas in the vial. The inlet hole in the shorter sharp end of the shorter outlet needle is positioned at the interface of the septum and vial interior to allow the gas to be forced from the vial via an outlet tube connected to the body of the devices. When liquid from the outlet tube is observed, the vial is quickly pulled away from the needles along the four guide posts.

The design of the device prevents airborne contaminants from entering the sample vial during sampling, and eliminates visible gas bubbles from the vial when properly operated. Its effect on other cumulative sample transfer biases, however, is unknown. The device was therefore tested using an all polytetrafluoroethylene (PTFE) dedicated bladder pump and discharge tubing to collect samples from wells known to be contaminated with trichloroethylene (TCE). The standard 3.5 mm silicone rubber and polytetrafluoroethylene (PTFE) septum was replaced with one 6.0 mm thick to reduce the potential loss of trichloroethylene (TCE) through the punctured septum once the vial is withdrawn from the needles and device.

Two 50 foot wells installed in identical geohydrologic settings were selected for the test. The last five feet of each well was screened and a dedicated polytetrafluoroethylene (PTFE) bladder pump suspended in the middle of the screen. One well was screened and cased with Schedule 40 polyvinylchloride (PVC), the other was constructed of Schedule 60 polytetrafluoroethylene (PTFE).

Both wells were purged of a specified volume of water based on previous field testing. After purging, ten consecutive samples were collected from each well, alternately filling the vial directly from the discharge line of the bladder pump and from a transfer device of the invention also connected to the same discharge line. The elapsed time between filling each 40 ml vial was about 1 minute.

For each directly collected fluid sample, the septum and cap were placed on the vial immediately after it was full. No gas bubbles were observed in either directly or transfer device collected samples. All samples were handled and stored in an identical manner until their delivery to the laboratory for analysis.

Results of the analysis for the two wells for trichloroethylene (TCE) was based on a reported detection limit of 0.5 ppb and an analytical error of 0.1 ppb. The results suggest that the sample concentration collected with the sample transfer device of the invention is higher than the concentration in the directly collected samples.

We claim:

1. A fluid sample transfer device comprising:
    a body having a bottom portion extending upwardly from a bottom side to an upper portion adjacent an upper side of the body, a fluid inlet passage extending through the body from an inlet end in the upper portion to an outlet end in the bottom portion, and a fluid outlet passage extending through the body from an inlet end adjacent the outlet end of the fluid inlet passage at the bottom side to an outlet end on another side of the body;
    a relatively long sharply pointed hollow needle having an upper inlet end fixed to the bottom portion, connected to and adapted to extend from the outlet end of the fluid passage a predetermined distance beyond the bottom side to a sharply pointed outlet end of the hollow needle adapted to pierce a self-sealing septum sealing an upper end of a vial and convey fluid into the vial at a point adjacent an inner bottom side of the vial to be filled when the upper end of the vial is positioned adjacent the bottom side of the body;
    a relatively short sharply pointed hollow fluid outlet needle connected to the inlet end of the fluid outlet passage in the bottom portion and extending a predetermined relatively short distance beyond the bottom side to a lower sharply pointed inlet end adapted to pierce and extend a short distance below the self sealing septum whereby fluid above the fluid being conveyed to and filling the vial may exhaust through the fluid outlet passage;
    connecting means on the upper portion of the body for connecting the inlet end of the fluid inlet passage to an outlet end of apparatus adapted to take and convey the fluid sample to the transfer device;
    guide means fixed to the bottom portion and extending a predetermined distance from the bottom side to an end thereof situated below the pointed outlet end of the long needle for holding and guiding the sealed vial and septum into and out of piercing sealing engagement with the long and short hollow needles, the guide means comprising
    a plurality of elongated guide rods spaced around and adapted for frictional engagement with an outer surface of the vial inserted in between the guide rods.

2. A fluid sample transfer device according to claim 1 wherein the connecting means comprises:
    a sealable tube and fitting assembly theradably connected to the upper portion and to the inlet end of the fluid inlet passage.

3. A fluid sample transfer device according to claim 2 further comprising:
    a valve movably mounted in and retained in sealing engagement with internal surfaces of a valve bore in the body and having a first passage movable with the valve into and out of alignment with the fluid inlet passage whereby flow of fluid may be selectively allowed to pass or be prevented from passing to the long hollow needle and into the vial, and a second passage in and movable with the valve into and out of alignment with an inlet end portion of the fluid inlet passage and an inlet end portion of a fluid filter passage in the body adapted for connection to a fluid filter whereby fluid entering the inlet end of the fluid inlet passage can, by moving the valve to the desired position, be selectively allowed to pass through the first passage of the valve to the hollow needle and into the vial or through the second passage of the valve and the fluid filter passage to the fluid filter and prevented by the valve from passing beyond the valve to both the filter and the long hollow needle and the vial.

4. A fluid sample transfer device according to claim 1 wherein the body and connecting means are made of virgin fluorocarbon material.

5. A fluid transfer device according to claim 4 wherein the body and connecting means are made of polytetrafluoroethylene.

6. A fluid transfer device according to claim 4 wherein the hollow needles are made of stainless steel.

7. A fluid transfer device according to claim 1 wherein the guide rods are made of stainless steel.

8. A fluid sample device according to claim 1 further comprising:
    a fluid sample vial inserted between and frictionally engaged and held by the guide means and having a tubular body extending upwardly from a bottom situated adjacently to and below the pointed end of the long inlet needle to an upper end portion having an upper surface extending around an inlet opening therein,
    a septum diaphram of resilient self sealing material extending over and sealing off the open inlet end of the vial and in sealing engagement with the long and short needles and situated above the pointed end of the short needle; and
    a cap with a central opening therein fastened to the upper inlet end portion of the vial and holding the self-sealing septum pierced by the needles in sealing engagement with the upper surface of the vial and the cap positioned adjacent the bottom side of the body and extending around the needles.

9. A fluid sample transfer device comprising:

a body having a bottom portion extending upwardly from a bottom side to an upper portion adjacent an upper side of the body, a fluid inlet passage extending through the body from an inlet end in the upper portion to an outlet end in the bottom portion, and a fluid outlet passage extending through the body from an inlet end adjacent the outlet end of the fluid inlet passage at the bottom side to an outlet end on another side of the body;

a relatively long sharply pointed hollow needle having an upper inlet end fixed to the bottom portion, connected to and adapted to extend from the outlet end of the fluid passage a predetermined distance beyond the bottom side to a sharply pointed outlet end of the hollow needle adapted to pierce a self-sealing septum sealing an upper end of a vial and convey fluid into the vial at a point adjacent an inner bottom side of the vial to be filled when the upper end of the vial is positioned adjacent the bottom side of the body;

a relatively short sharply pointed hollow fluid outlet needle connected to the inlet end of the fluid outlet passage in the bottom portion and extending a predetermined relatively short distance beyond the bottom side to a lower sharply pointed inlet end adapted to pierce and extend a short distance below the self sealing septum whereby fluid above the fluid being conveyed to and filling the vial may exhaust through the fluid outlet passage;

connecting means on the upper portion of the body for connecting the inlet end of the fluid inlet passage to an outlet end of apparatus adapted to take and convey the fluid sample to the transfer device comprising a tubular upper portion having an internal fluid inlet bore connected to the fluid inlet passage and adapted to be inserted into and sealingly engage inner surfaces of an outlet bore in an outlet end portion of a bailer including a check valve containing a fluid sample to be transferred to the vial; and an elongated drain pin with a fluid passage inserted in the internal fluid inlet bore and adapted to extend upwardly above the tubular upper portion, engage and raise the check valve in the bailer off its seat whereby fluid may flow into and through the body of the long hollow needle and into the vial.

10. A fluid sample transfer device according to claim 9 further comprising:

a valve movably mounted and retained in sealing engagement with internal surfaces of a valve bore in the body and having a passage movable with the valve into and out of alignment with the fluid passage in the body, whereby flow of fluid may be selectively allowed to pass or be prevented from passing through the fluid passage, the hollow needle, and into the vial.

* * * * *